(12) United States Patent
Hara et al.

(10) Patent No.: US 8,781,200 B2
(45) Date of Patent: Jul. 15, 2014

(54) CT IMAGE PROCESSING DEVICE AND CT IMAGE PROCESSING METHOD

(75) Inventors: Yukihiro Hara, Hino (JP); Takafumi Koike, Kamakura (JP)

(73) Assignee: Rigaku Corporation, Tokyo (JP)

( * ) Notice: Subject to any disclaimer, the term of this patent is extended or adjusted under 35 U.S.C. 154(b) by 149 days.

(21) Appl. No.: 13/419,219

(22) Filed: Mar. 13, 2012

(65) Prior Publication Data

US 2012/0237099 A1 Sep. 20, 2012

(30) Foreign Application Priority Data

Mar. 14, 2011 (JP) ................................. 2011-055494

(51) Int. Cl.
*G06K 9/00* (2006.01)

(52) U.S. Cl.
USPC ........................................................ 382/131

(58) Field of Classification Search
USPC ................. 382/100, 128, 129, 130, 131, 132; 128/922; 378/4–27
See application file for complete search history.

(56) References Cited

U.S. PATENT DOCUMENTS

| | | | | |
|---|---|---|---|---|
| 7,313,215 B2 * | 12/2007 | Hsieh et al. | ...................... | 378/15 |
| 7,426,255 B2 * | 9/2008 | Miyazaki et al. | .................. | 378/8 |
| 7,460,699 B2 * | 12/2008 | O'Donnell et al. | ............ | 382/128 |
| 7,734,005 B2 * | 6/2010 | Hsieh et al. | ......................... | 378/8 |
| 7,778,385 B2 * | 8/2010 | Hsieh et al. | ......................... | 378/8 |
| 8,005,283 B2 * | 8/2011 | John et al. | ..................... | 382/130 |
| 8,160,675 B2 * | 4/2012 | Jaffray et al. | ................. | 600/425 |
| 2005/0169509 A1 * | 8/2005 | Grasslin et al. | ............... | 382/130 |
| 2006/0140337 A1 * | 6/2006 | Miyazaki et al. | .................. | 378/8 |
| 2008/0101532 A1 * | 5/2008 | Tkaczyk et al. | .................. | 378/8 |
| 2011/0274334 A1 * | 11/2011 | Zhu et al. | ...................... | 382/132 |

FOREIGN PATENT DOCUMENTS

| | | |
|---|---|---|
| JP | 2006-346263 A | 12/2006 |
| JP | 2008-228828 A | 10/2008 |
| JP | 2008-228829 A | 10/2008 |

OTHER PUBLICATIONS

Dinkel et al., "Intrinsic gating for small-animal computed tomography: a robust ECG-less paradigm for deriving cardiac phase information and functional imaging", Circulation Cardiovascular Imaging, Journal of the American Heart Association, Nov. 2008, vol. 1, pp. 235-243.

* cited by examiner

*Primary Examiner* — Anand Bhatnagar
(74) *Attorney, Agent, or Firm* — Birch, Stewart, Kolasch & Birch, LLP

(57) ABSTRACT

A CT image processing device 5 which processes projection data in synchronization with a periodic motion of a portion of a subject includes an ROI calculation unit 36 which calculates specific information on an ROI for synchronization for each scanning angle so as to track the target portion of the subject. As a result, a strong synchronization signal is obtained, a characteristic amount in which breathing beat and heartbeat sufficiently appear can be measured, and simple synchronization processing is made possible by using the projection data. A dedicated device for obtaining the heartbeat or breathing beat such as ECG and a respiratory measuring device is not required, and a heartbeat signal and a breathing beat signal can be obtained from an ROI signal of the projection data. As a result, blurring on an image caused by the heartbeat can be eliminated, and an image quality is extremely improved.

13 Claims, 20 Drawing Sheets

CT IMAGE PROCESSING DEVICE AND CT IMAGE PROCESSING METHOD

BACKGROUND OF THE INVENTION

1. Field of the Invention

The present invention relates to a CT image processing device and a CT image processing method in which a portion of a subject is scanned by an X-ray CT device in synchronization with a periodic motion thereof and obtained projection data is processed so as to reconstruct an image.

2. Description of the Related Art

X-ray CT scanning is effective for in vivo observation of an animal such as a mouse and a rat. However, animals cannot stop breathing during CT scanning in accordance with an instruction of an operator as humans do. Moreover, hearts cannot stop during biological scanning. Therefore, images of hearts, lungs and neighboring organs such as livers are blurred by influences of heartbeat and breathing, and the X-ray CT is not suitable for observation or inspection of fine portions.

An X-ray CT device capable of breathing beat synchronized scanning has been developed because of the above-described circumstances. In devices of Japanese Unexamined Patent Application Publication No. 2008-228828 (Patent Document 1) and Japanese Unexamined Patent Application Publication No. 2008-228829 (Patent Document 2), for example, a region of interest is set so as to include a region of a periodic motion portion of a subject, and a characteristic amount obtained by integration over the region of interest is calculated as a synchronization signal of the periodic motion of the subject. Then, rotation of a gantry is controlled by shifting a phase using the synchronization signal of the periodic motion, to perform X-ray CT scanning, and interpolation processing is performed with data scanned in a plurality of rotations.

Moreover, in a controller described in Dinkel et al, Intrinsic Gating for Small-Animal Computed Tomography A Robust ECG-Less Paradigm for Deriving Cardiac Phase Information and Functional Imaging, Journal OF THE American Heart Association, USA, American Heart Association, Circ Cardiovasc Imagin 2008; 1; 235-243 (Non-patent Document 1), breathing beat is obtained by placing a pressure sensor in the vicinity of a subject chest portion, while electrodes are punctured on the both shoulders and a foot portion of a subject, and ECG measurement is made so as to obtain a heartbeat signal. Then, several sessions of CT scanning are performed while a phase is shifted with respect to the breathing beat, CT angle data with the same phase is selected and organized into single CT data, and image reconstruction of the synchronous CT data is executed.

On the other hand, some X-ray CT scanning devices calculate a position of a region in accordance with a scanning angle on the basis of the region set in a scanned image. In an X-ray blood vessel imaging device described in Japanese Unexamined Patent Application Publication No. 2006-346263 (Patent Document 3), a gate area is stored with respect to an inspection portion and a scanning angle, and the stored gate area corresponding to the inspection portion and the scanning angle is set for each scanned image. At that time, gate area information is created for the set scanning angle from the gate area information registered for the angles nearby.

SUMMARY OF THE INVENTION

As described above, the devices in Patent Documents 1 and 2 prevent blurring of an image due to breathing beat by performing X-ray CT scanning while controlling rotation of the gantry by shifting the phase. However, this type of synchronization calculating device needs mechanical control of the gantry in accordance with the periodic motion of the portion. Moreover, small animals have fast heartbeat, and it is difficult to substantially eliminate the influence. Furthermore, the controller described in Non-patent Document 1 can eliminate the influence of the heartbeat, but a work load of an operator is large, and since puncture of electrodes is involved, safety of the operator cannot be ensured. Moreover, a load is applied to the subject. Scanning time tends to be long, and an image quality of the portion influenced by the heartbeat cannot be considered to be sufficient. Moreover, artifacts (false images) can be easily generated by puncture of electrodes, and ECG is expensive.

The X-ray blood vessel imaging device described in Patent Document 3 creates gate area information at the scanning angle set from the gate area information at the neighboring angles, but its purpose is to maintain contrast of the image in the region and is largely different from elimination of the influence of the periodic motion of the portion.

The present invention was made in view of the above circumstances and has an object to provide a CT image processing device and a CT image processing method that can extract a synchronization signal from projection data obtained by CT scanning and can obtain a synchronized CT image with simple synchronization processing. Fluoroscopic data refers to X-ray data transmitted through a subject by a predetermined rotation angle and detected, and a fluoroscopic image refers to an image displaying the fluoroscopic data as a fluoroscopic image. Moreover, the projection data refers to X-ray data transmitted through the subject by rotary scanning and measured by a detector, and CT image data refers to image data reconstructed by using the projection data.

(1) In order to achieve the above object, a CT image processing device according to the present invention is a CT image processing device which processes X-ray projection data in synchronization with a periodic motion of a portion of a subject, and includes an ROI calculating unit configured to calculate specific information on ROI for synchronization for each scanning angle so as to track the portion of the subject to be synchronized with.

With this configuration, a strong synchronization signal is obtained and a characteristic amount in which heartbeat and breathing beat sufficiently appear can be measured, and simple synchronization processing by using projection data is made possible. Dedicated devices for obtaining heartbeat or breathing beat such as ECG and respiratory measuring device are not required, and a heartbeat signal and a breathing beat signal can be obtained from an ROI signal of the projection data easily and with a low cost. As a result, blurring in an image caused by heartbeat can be eliminated, and the image quality is extremely improved. For example, cardiac synchronized images of both diastole and systole can be obtained and utilized for cardiac function inspections, for example. Then, diagnoses of hearts, lungs, livers and peripheral organs are reliably improved.

Moreover, puncture of a needle is no longer necessary, and workability of heartbeat synchronized scanning and breathing beat synchronized scanning can be improved. Since a synchronization signal is obtained without using an ECG electrode, an accident in puncture can be eliminated. As described above, work safety of an operator can be ensured, and a load on a subject can be alleviated. Moreover, occurrence of artifacts caused by punctured electrode can be prevented.

(2) Moreover, the CT image processing device according to the present invention is characterized in that the ROI calculating unit calculates the specific information of ROI for synchronization for the projection data of other scanning angles on the basis of the ROI for synchronization set for fluoroscopic data of a plurality of scanning angles. Thereby, the ROI for synchronization can be specified for each scanning angle so as to track the portion of the subject which is a target.

(3) Moreover, the CT image processing device according to the present invention is characterized in that the ROI calculating unit calculates a position and a shape of the ROI for synchronization by referring to the position of a rotation center of X-ray irradiation on the projection data. Thereby, the ROI for synchronization can be set at each scanning angle so as to track the target portion to be synchronized with and can be processed reliably in synchronization with the periodic motion of the portion.

(4) Moreover, the CT image processing device according to the present invention is characterized in that the ROI calculating unit calculates the ROI for synchronization of projection data of other scanning angles on the basis of the ROI for synchronization set for projection data of two scanning angles forming an angle of 90° with each other. Thereby, if the ROI for synchronization at another angle is to be calculated, overlooking of a synchronization signal can be reduced. The angle formed by each ROI for synchronization is preferably 90° but the angle may be set for each of projection data of two scanning angles of 60° or more and 120° or less.

(5) Moreover, the CT image processing device according to the present invention is characterized by further including a breathing synchronized processing unit configured to sort each projection data into a predetermined phase segment of breathing beat on the basis of a relationship between the scanning angle and a characteristic amount of the ROI for synchronization. Thereby, for example, the projection data can be sorted into a segment other than diastole of the breathing beat.

(6) Moreover, the CT image processing device according to the present invention is characterized in that the heartbeat synchronized processing unit calculates a moving average value of the characteristic amount of the ROI for synchronization with respect to the scanning angle for the projection data sorted into the predetermined phase segment of breathing beat and sorts and extracts the projection data on the basis of the moving average value. Thereby, data for diastole and data for systole of the breathing beat can be clearly separated. Since the breathing beat changes steeper than the heartbeat, the breathing beat is not influenced by the heartbeat.

(7) Moreover, the CT image processing device according to the present invention is characterized by further including a heartbeat synchronized processing unit configured to sort and extract the projection data sorted into the predetermined phase segment of breathing beat into a predetermined phase segment of heartbeat on the basis of a relationship between the scanning angle and the characteristic amount of the ROI for synchronization. Thereby, the sorted data can be further sorted into a segment of diastole of the heartbeat and extracted.

(8) Moreover, the CT image processing device according to the present invention is characterized in that the heartbeat synchronized processing unit calculates a moving average value of the characteristic amount of the ROI for synchronization with respect to the scanning angle for the projection data sorted into the predetermined phase segment of breathing beat and sorts and extracts the projection data on the basis of the moving average value. By using the moving average value as a basis, the data of the diastole and the data of the systole of the heartbeat can be separated. A quaternary value, for example, is used for the moving average.

(9) Moreover, the CT image processing device according to the present invention is characterized by further including an image reconstruction unit configured to reconstruct CT image data by the projection data sorted into the predetermined phase segment of breathing beat or heartbeat. Thereby, a clear CT image data can be obtained also for the portion periodically moving by using the projection data sorted into the phase segment of a specific breathing beat or a phase segment of the heartbeat.

(10) Moreover, the CT image processing device according to the present invention is characterized in that the image reconstruction unit reconstructs the CT image by interpolating the projection data missing due to the sorting of the projection data with projection data at the adjacent scanning angle. Thereby, the artifact caused due to lack of the projection data can be reduced.

(11) Moreover, the CT image processing device according to the present invention is characterized in that the image reconstruction unit uses the projection data averaged for a plurality of pieces of data having the scanning angles close to each other for reconstruction of the CT image data as projection data with respect to the averaged scanning angle. Thereby, high-speed CT image reconstruction calculation processing can be executed.

(12) Moreover, the CT image processing device according to the present invention is characterized by further including an ROI setting unit configured to store the ROI for synchronization set for the projection data of a plurality of scanning angles in association with the projection data during scanning. Since the ROI for synchronization can be set at the plurality of scanning angles, the ROI for synchronization at other angles can be calculated by using the set ROI for synchronization.

(13) Moreover, a CT image processing method according to the present invention is a CT image processing method including the step of calculating specific information on ROI for synchronization is executed for each scanning angle so as to track the portion of the subject to be synchronized with.

Thereby, simple synchronization processing is made possible by using projection data. A heartbeat signal and a breathing beat signal can be obtained from the ROI signal of the projection data without requiring dedicated devices for obtaining heartbeat and breathing beat such as ECG and a respiratory measuring device. As a result, blurring of an image caused by heartbeat can be eliminated, and the image quality is extremely improved. Moreover, cardiac synchronized images both for diastole and systole can be obtained and used for cardiac functional tests.

According to the present invention, the ROI for synchronization can be set at other scanning angles on the basis of the ROI for synchronization set at a plurality of scanning angles. As a result, a synchronization signal can be finely obtained by using the projection data, simple synchronization processing is made possible, and a burden on an operator can be alleviated. Moreover, diagnoses of hearts, lungs, livers and peripheral organs are reliably improved.

DETAILED DESCRIPTION OF THE INVENTION

Figure 1:
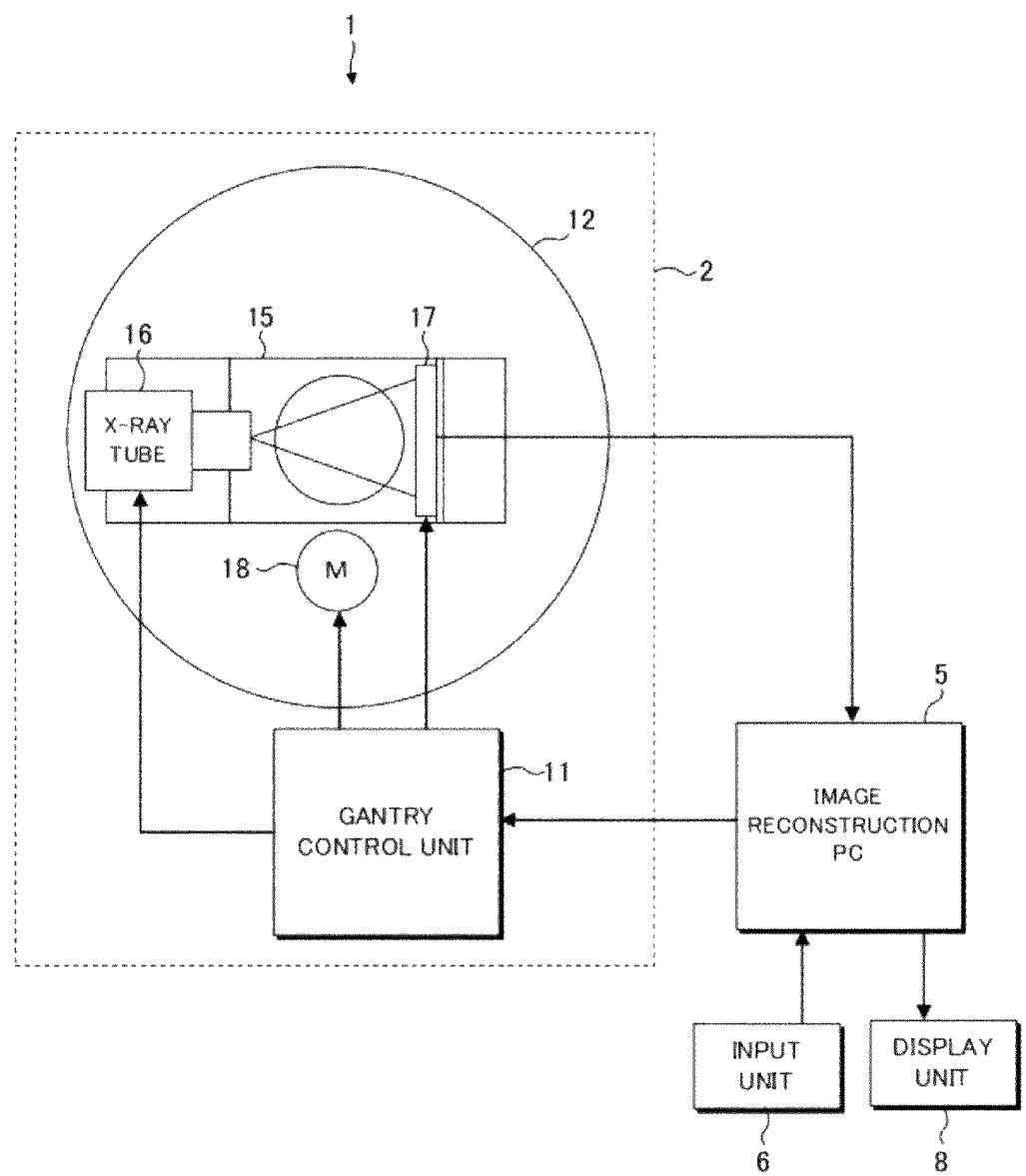
FIG. 1 is an outline diagram illustrating an X-ray CT device according to the present invention.

An embodiment of the present invention will be described below by referring to the attached drawings. For facilitation of understanding of the explanation, the same reference numerals are given to the same constituent element in each figure, and duplicated explanation will be omitted.

(Configuration of X-ray CT Device)

FIG. 1 is an outline diagram of an X-ray CT device 1. As illustrated in FIG. 1, the X-ray CT device 1 includes a scanning unit 2, an image reconstruction PC 5 (CT image processing device), an input unit 6, and a display unit 8. The scanning unit 2 has a gantry control unit 11 and a gantry 12 and performs X-ray CT of a held subject by rotating the gantry 12. The scanning unit 2 performs CT scanning at calculated timing to start CT scanning and scans projection data of the subject. The scanned CT data is transmitted to the image reconstruction PC 5. Also, the scanning unit 2 is capable of CT scanning in synchronization with breathing and scanning of the projection data of the subject.

The gantry 12 is provided rotatable around the subject for obtaining fluoroscopic data of the subject at a predetermined rotation angle and for obtaining the projection data through rotating scanning. The gantry 12 includes a rotating arm 15, an X-ray tube 16, a detector 17, and an arm rotating motor 18. The X-ray tube 16 and the detector 17 are fixed to the rotating arm 15. The rotating arm 15 is installed in the gantry 12 rotatably around a point between the X-ray tube 16 and the detector 17.

The X-ray tube 16 generates and projects X-ray toward the detector 17. The detector 17 has a light receiving surface which receives the X-ray and is formed having the shape of a panel. The X-ray is projected from the X-ray tube 16, transmitted through the subject and detected by the detector 17. The arm rotating motor 18 rotates the entire gantry 12 by rotating the rotating arm 15. The arm rotating motor 18 can rotate the gantry 12 at a set speed during CT scanning. Moreover, when the scanning is finished, the arm rotating motor 18 can rotate the gantry 12 in the reverse direction to an original position. The X-ray CT device 1 has been described as an arm-type device, but application of the present invention is not limited to this type.

The X-ray CT device 1 can collect a large amount of data at a high speed by using the high-speed detector 17 and can reduce scanning time. Moreover, the device can reduce an influence of body movement by high-speed data collection. A frame rate is preferably 30 fps or more and more preferably 100 fps or more. By setting the frame rate at 30 fps or more, scanning of diastole and systole of heartbeat of a small animal like a mouse in the same frame can be prevented. Also, projection data of 3600 to 14400 frames in total are preferably obtained in advance. However, the synchronization processing can be executed only by means of software without requiring special hardware.

The image reconstruction PC 5 (CT image processing device) obtains the scanned projection data and calculates a characteristic amount as a synchronization signal of breathing beat or heartbeat on the basis of the projection data. Then, the PC 5 reconstructs three-dimensional CT image data by using the breathing synchronization signal. The image reconstruction PC 5 also has a function of transmitting a scanning condition and the like to the scanning unit 2 and controlling an operation of the scanning unit 2. The input unit 6 such as a keyboard, a mouse and the like receives an input from a user and transmits the input signal to the image reconstruction PC 5.

The display unit 8 such as a display device displays a fluoroscopic image and an obtained synchronization signal. Also, the display unit 8 displays the projection data during CT scanning and displays CT image data after image reconstruction. The gantry control unit 11 receives an instruction from the image reconstruction PC 5, controls the rotation of the gantry 12 at an instructed speed and controls CT scanning by means of the X-ray tube 16 and the detector 17.

(Configuration of Image Reconstruction PC)

Figure 2:
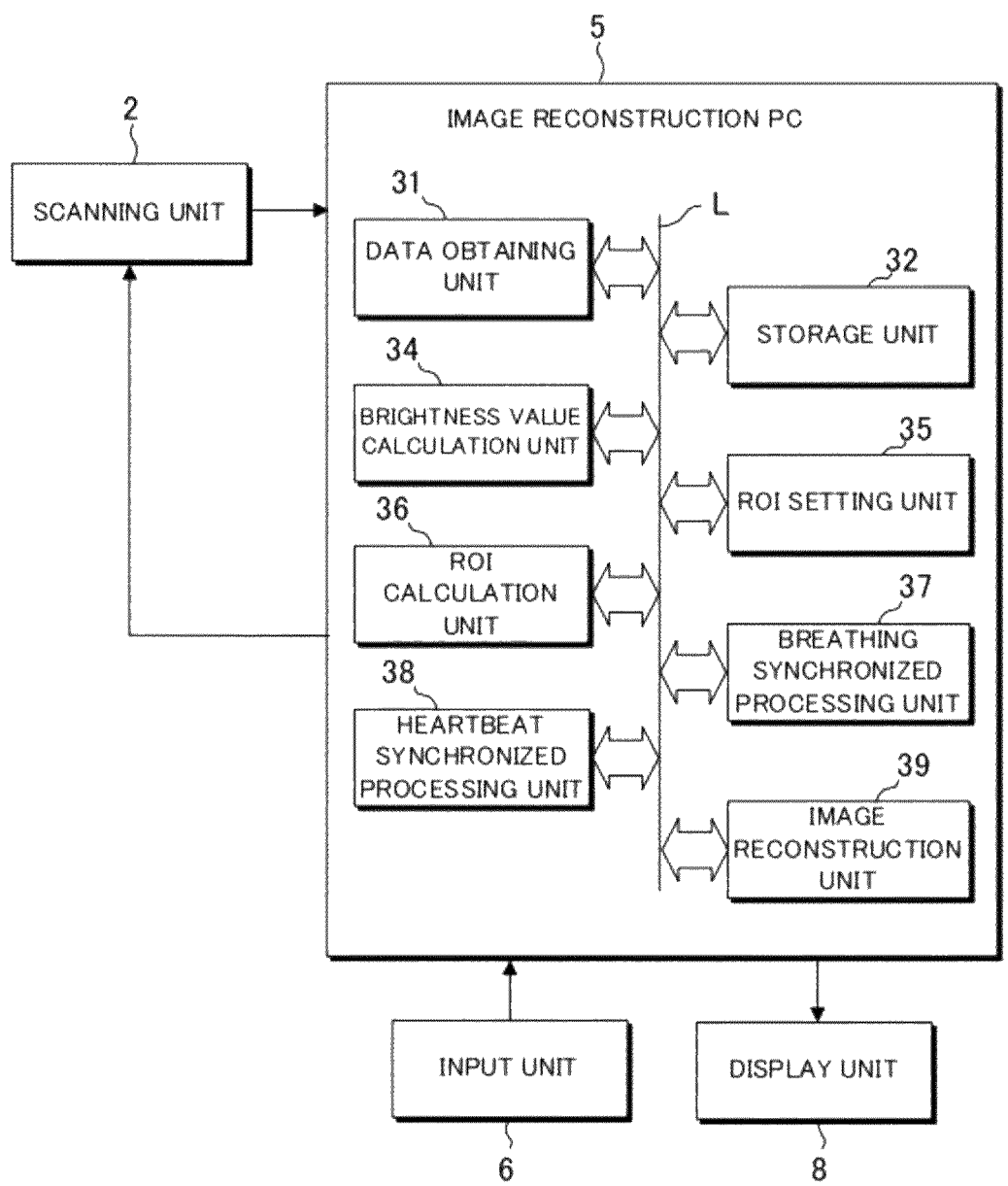
FIG. 2 is a block diagram illustrating the X-ray CT device according to the present invention.

Subsequently, the function of image processing will be described in more detail. FIG. 2 is a block diagram of the X-ray CT device 1. As illustrated in FIG. 2, the image reconstruction PC 5 receives the input of the user from the input unit 6 such as a keyboard, a mouse and the like. On the other hand, the image reconstruction PC 5 displays the fluoroscopic image, an input screen and the like on the display unit 8 such as a display device. During scanning, the image reconstruction PC 5 transmits control information inputted from the user to the scanning unit 2.

Moreover, the image reconstruction PC 5 includes a data obtaining unit 31, a storage unit 32, a brightness value calculation unit 34 (characteristic amount calculation unit), an ROI setting unit 35, an ROI calculation unit 36, a breathing synchronized processing unit 37, a heartbeat synchronized processing unit 38, and an image reconstruction unit 39 and processes the projection data in synchronization with a periodic motion of a portion of the subject. Each unit can transmit/receive information through a control bus L. The image reconstruction PC 5 is substantially composed of a CPU and a memory or a hard disk or the like.

The data obtaining unit 31 obtains fluoroscopic data and projection data of the subject from the scanning unit 2. The storage unit 32 stores the obtained projection data of the subject. Also, the storage unit 32 stores a brightness value calculated by the brightness value calculation unit 34.

The brightness value calculation unit 34 integrates the brightness values in an ROI (Region of Interest) for synchronization set for the obtained projection data and divides the brightness value by the number of pixels of the ROI for synchronization. As a result, an average value (characteristic amount) of the brightness value can be calculated as a breathing synchronization signal. The characteristic amount does not necessarily have to be a brightness value but is enough to be any value corresponding to an integrated value of a certain region. The calculation of the ROI for synchronization is made during or after collection of the data. The ROI for synchronization has an application different from an ROI for observation and is used for grasping a strong signal of a periodic motion.

The ROI setting unit 35 stores the ROI for synchronization set for fluoroscopic data of a plurality of angles in association with a scanning angle at fluoroscopy. The ROI for synchronization is set by input by a user from the input unit 6. The plurality of scanning angles are preferably two scanning angles which form an angle of 60° or more and 120° or less with each other and more preferably two angles orthogonal to each other. As a result, if the ROI for synchronization of another angle is to be calculated, a setting error can be reduced. The ROI for synchronization may be set for three or more scanning angles.

At this time, the image reconstruction PC 5 preferably displays the ROI for synchronization for setting and displays the characteristic amount of the X-rays in the ROI for synchronization for setting on a real time basis. For example, the user can determine appropriateness of the setting of the ROI for synchronization on the basis of whether a strong signal has been obtained or not by checking the display of graph of the characteristic amount.

As described above, the image reconstruction PC 5 can set the ROI for synchronization even at another scanning angle on the basis of the ROI for synchronization set at a plurality of scanning angles. As a result, a characteristic amount sufficiently expressing heartbeat and breathing beat can be measured, and simple synchronization processing is made possible by using projection data. A dedicated device for detecting heartbeat or breathing beat such as ECG, a respiratory measuring device and the like is no longer required, and a heartbeat signal and a breathing beat signal can be obtained from the ROI for synchronization of the projection data. Thus, blurring of an image caused by heartbeat can be eliminated, and the image quality is extremely improved. Moreover, cardiac synchronized images both for diastole and systole can be obtained and used for cardiac functional tests.

Moreover, since ECG measurement is not involved, puncture of a needle is no longer required, workability of heartbeat synchronized scanning and breathing beat synchronized scanning is improved, and no accident is caused by puncture. As described above, working safety of an operator can be ensured, and a burden on a subject can be alleviated.

The ROI calculation unit 36 calculates specific information of the ROI for synchronization for the projection data at another scanning angle on the basis of the ROI for synchronization set for the fluoroscopic data of a plurality of scanning angles. As described above, the ROI for synchronization can be specified so as to track the portion to be synchronized with by interpolating the ROI for synchronization for an angle other than the angle for which the ROI for synchronization has been set.

The heart is located in the depth on the left on the front from view of the subject, and if the subject is placed on a stage and rotationally scanned, the heart moves in the shape of an ellipse. Therefore, a synchronization signal of the heart cannot be sufficiently captured by the fixed ROI. However, the movement can be tracked by using the calculation processing of the above-described ROI for synchronization. As above, a strong synchronization signal for the heartbeat can be detected. At the calculation, the position and the shape of the ROI for synchronization is calculated as its specific information by referring to the position of the rotation center of the X-ray irradiation on the projection data. Details of the procession for interpolating the ROI for synchronization will be described later.

The breathing synchronized processing unit 37 sectionalizes each projection data to a predetermined phase section of a breathing beat and extracts it on the basis of the relationship between the scanning angle and the characteristic amount of the ROI for synchronization. The predetermined phase section of the breathing beat is systole and diastole of a lung, for example. Specifically, the characteristic amount of the ROI for synchronization is differentiated by the scanning angle, and the projection data is sorted and extracted on the basis of a predetermined threshold value. Since a motion of a diaphragm caused by the breathing beat appears in the characteristic amount as a steep change with amplitude larger than haertbeat, the differential values are largely different between the diastole and the systole of the lung. The data can be separated between the diastole and the systole of the lung by using this.

As described above, the projection data can be sorted to a phase section of the breathing beat and a phase section of the heartbeat and extracted. For example, the projection data is sorted to a section other than the diastole of the lung and the sorted data can be further sorted into a section of the diastole of the heartbeat. Since the breathing beat is steeper than the heartbeat, the breathing beat is hardly affected by the heartbeat.

The heartbeat synchronized processing unit 38 sectionalizes the projection data sorted to a predetermined breathing beat phase section in the breathing synchronized processing unit 37 into a predetermined heartbeat phase section on the basis of the relationship between the scanning angle and the characteristic amount of the ROI for synchronization. The predetermined heartbeat phase section is the diastole and the systole of the heart, for example. The sectionalization processing is preferably executed such that a moving average value of the characteristic amount of the ROI for synchronization to the scanning angle is calculated and the projection data is sorted on the basis of the moving average value. By using the moving average value as a reference, the data of the diastole of the heartbeat can be separated from the data of the systole. The moving averaging is executed by using a quaternary value, for example.

The image reconstruction unit 39 reconstructs the three-dimensional CT image data by the projection data sorted into the predetermined breathing beat or heartbeat phase section. As a result, a clear CT reconstructed image can be obtained also for the portion periodically moving by using the projection data sorted into a specific breathing beat phase section and the heartbeat phase section. The image reconstruction unit 39 extracts required projection data and reconstructs the CT image data with the data for one rotation of the gantry subjected to the synchronization processing. As a result, CT image data with no artifact and less blurring can be obtained.

In the reconstruction processing, the projection data missing by the sectionalization of the projection data is preferably interpolated by the projection data in the vicinity of the scanning angle so as to reconstruct the CT image data. As a result, clear CT image data can be obtained efficiently. For example, the projection data averaged for a plurality of pieces of data with nearby scanning angles is used for reconstruction of the CT image data as projection data for the averaged scanning angle. The reconstruction is preferably executed on the basis of approximately 1000 frames of projection data. That is because if there are too much projection data to be calculated, calculation processing load becomes large. In that case, the CT image data is reconstructed by using single usable projection data to 16 pieces of projection data, for example.

(Use Procedure and Device Operation)

Figure 3:
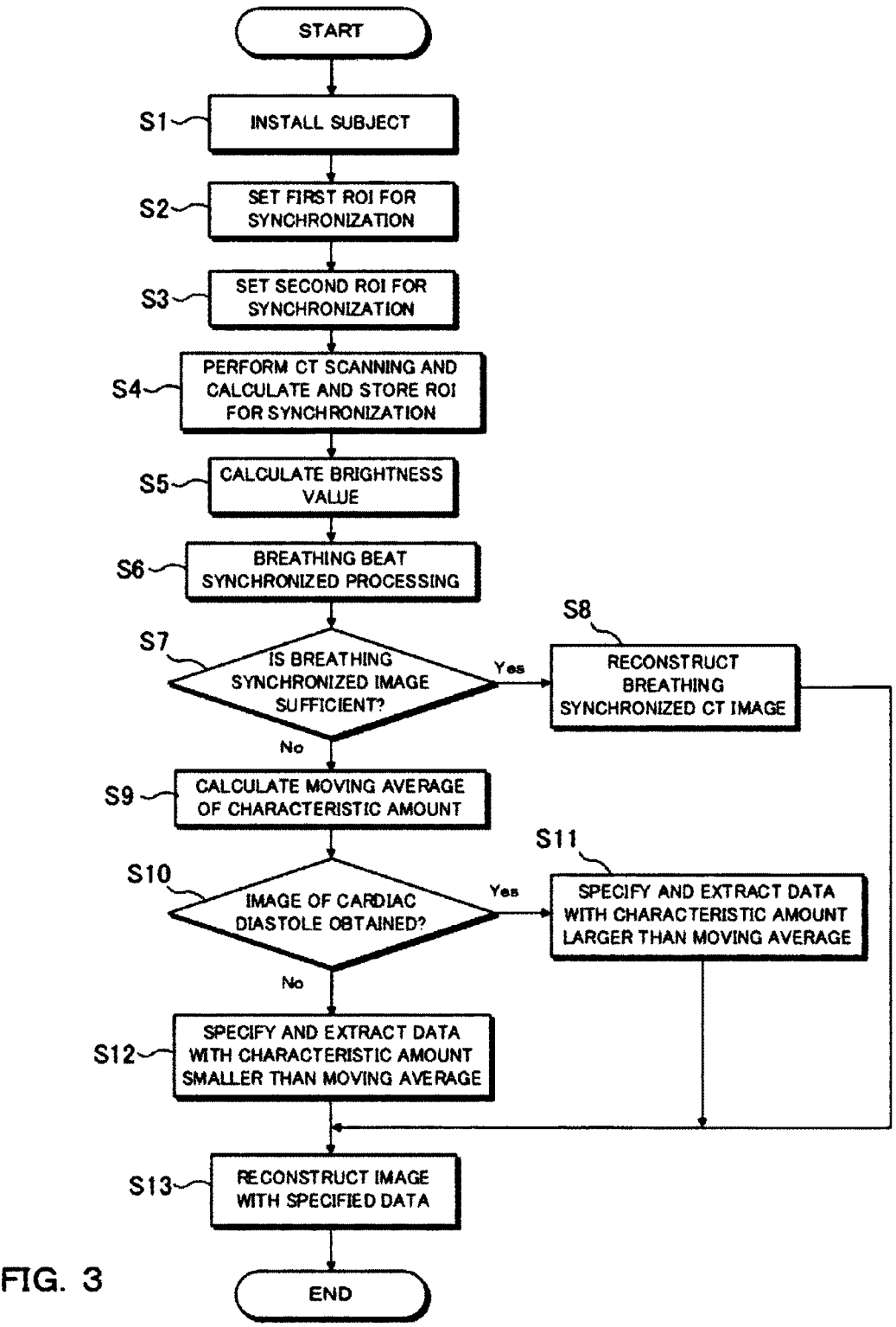
FIG. 3 is a flowchart illustrating a use procedure and an operation of the X-ray CT device according to the present invention.

Subsequently, an example of a use procedure and an operation of the X-ray CT device 1 configured as above will be described. FIG. 3 is a flowchart illustrating the use procedure and the operation of the X-ray CT device 1.

First, a user installs a subject such as a mouse, a rat and the like on a bed provided in the scanning unit 2 (Step S1). Then, the X-rays are irradiated to the subject by prior scanning so as to obtain fluoroscopic data. The prior scanning for approximately 5 seconds is sufficient, and the gantry is not rotated. At this time, processing is executed immediately, a breathing synchronization signal is calculated, and a graph is displayed. The ROI for synchronization is set in a region indicating the heart portion of the obtained fluoroscopic data (Step S2). At this time, the X-ray CT device 1 receives information of a position and a shape for specifying the ROI for synchronization from the user. For example, a rectangular ROI for synchronization can be set by setting a diagonal line by operating drag-and-drop using a mouse, for example. The user preferably sets the ROI for synchronization so as to include opposing side walls of the heart on the head side from the diaphragm. The shape of the ROI for synchronization does not necessarily have to be a rectangle.

Subsequently, the X-ray irradiation is performed at an angle orthogonal to the scanning angle at which the ROI for synchronization is set at Step S2, and the ROI for synchronization is set at the heart portion of the obtained projection data (Step S3). Then, the X-ray CT scanning of the subject is conducted so as to obtain the projection data, and the position and the size of the ROI for synchronization are calculated for the angle other than the scanning angle for which the ROI for synchronization is set for the scanned projection data (Step S4). That is, the X-ray CT device 1 receives the input to start scanning from the user, rotates the gantry, starts the scanning, scans the projection data of the subject in accordance with a trigger signal, and calculates and stores the position and the size of the ROI for synchronization for each projection data.

Then, the X-ray CT device 1 calculates an average value of a count value (brightness value) in the ROI for synchronization (Step S5). The average value of the count values can be calculated by integrating the count values in the ROI and dividing the result by the number of pixels. A differential value by the scanning angle of the characteristic amount of the ROI for synchronization is acquired for the projection data of each scanning angle obtained as above, and the projection data of the systole of the lung is specified (Step S6).

Subsequently, the user determines whether a breathing synchronized image is sufficient or a heartbeat synchronization image is also required and inputs an instruction (Step S7). If the X-ray CT device 1 receives an instruction that breathing synchronization image is sufficient, the X-ray CT device 1 specifies the projection data sorted into the lung systole by the breathing synchronization for reconstruction of a three-dimensional CT image data (Step S8) and ends the processing.

On the other hand, if an instruction to obtain also the heartbeat synchronized image is received, the X-ray CT device 1 acquires a moving average for the projection data specifies as the data of lung systole (Step S9). Then, the user specified which of the diastole and systole of the heart is to be obtained, and the X-ray CT device 1 determines if the data to be obtained is the diastole data or systole data of the heart in accordance with the specification (Step S10).

If the diastole data of the heart is to be used, the CT image is reconstructed by the projection data of the scanning angle in which the characteristic amount of the ROI for synchronization is larger than the moving average value (Step S11). Alternatively, if the systole data of the heart is to be used, the projection data of the scanning angle in which the characteristic amount of the ROI for synchronization is smaller than the moving average value (Step S12). The CT image is reconstructed by the projection data of the lastly specified scanning angle (Step S13), and the processing is finished.

(Setting of ROI for Synchronization)

Figure 4:
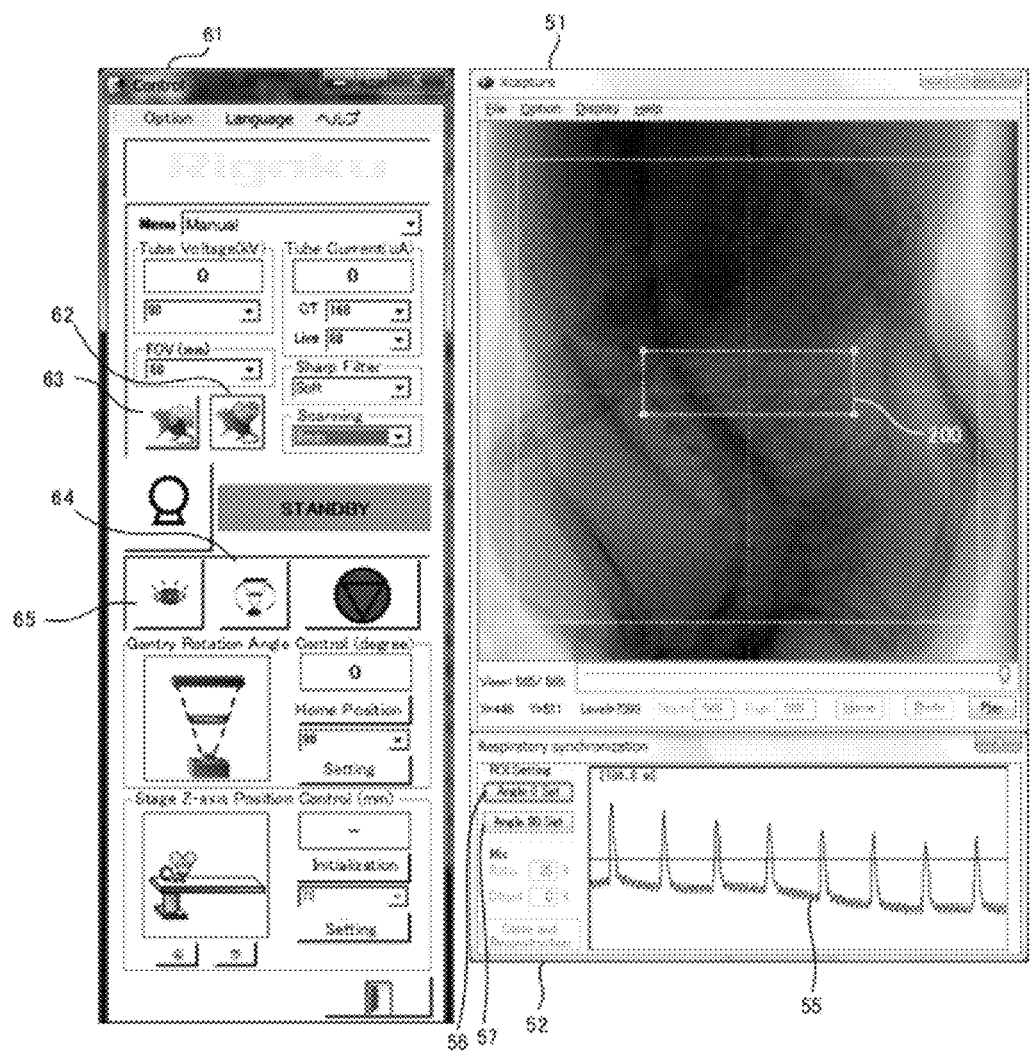
FIG. 4 is a view illustrating a setting screen of ROI for synchronization.

Subsequently, the details of the setting procedure of the ROI for synchronization will be described. FIG. 4 is a view illustrating a setting screen of the ROI for synchronization. As illustrated in FIG. 4, the display unit 8 displays a fluoroscopic image screen 51, a graph display screen 52, and a control panel 61. The fluoroscopic image screen 51 displays a fluoroscopic image and the position and the size of an ROI 200 for synchronization. The graph display screen 52 displays a characteristic amount graph 55, a determination button 56 for the ROI for synchronization at the scanning angle of 0°, and a determination button 57 for the ROI for synchronization at the scanning angle of 90°.

In the characteristic amount graph 55, a large peak occurring with a long period on a gentle waveform by rotation and s small peak occurring with a short period between the large peaks can be observed. The large peaks express the lung diastole in the breathing beat, while the small peaks express the heart diastole in the heartbeat. The peak in the breathing beat is larger than the heartbeat peak by approximately ten times and changes rapidly. The user sets the ROI 200 for synchronization with the position and the size that can capture not only the breathing beat but also the heartbeat signals sufficiently largely while observing the characteristic amount graph 55.

The control panel 61 displays a selection button 63 for breathing synchronized processing, a selection button 62 for heartbeat synchronized processing, a fluoroscopic start button 65, and a CT start button 64, and the user can instruct scanning or processing by operating these GUIs.

Figure 5:
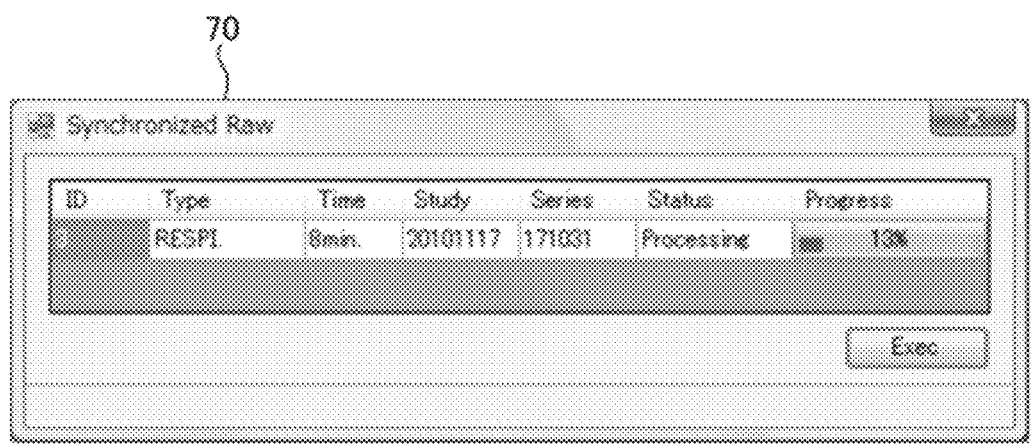
FIG. 5 is a view illustrating a synchronization processing display screen.

When the ROI for synchronization is to be set, first, fluoroscopic image scanning is started. Then, the frame of the ROI for synchronization is moved and adjusted at the scanning angle of 0°, and the ROI 200 for synchronization is determined by the determination button 56 for ROI for synchronization. Similarly, the frame of the ROI 200 for synchronization is moved and adjusted at the scanning angle of 90° and the ROI for synchronization is determined by the ROI determination button 57 for synchronization. Then, the fluoroscopic image scanning is finished, and the CT scanning button is pressed. Then, the image reconstruction PC 5 starts performing of CT scanning and obtains the projection data and the value of the ROI for synchronization. Subsequently, the synchronization processing software is automatically started, and the projection data sorted by synchronization is extracted. FIG. 5 is a view illustrating a synchronization processing display screen. If "Progress" display on the screen proceeds to 100%, the routine proceeds to the image reconstruction processing.

Figure 6A:
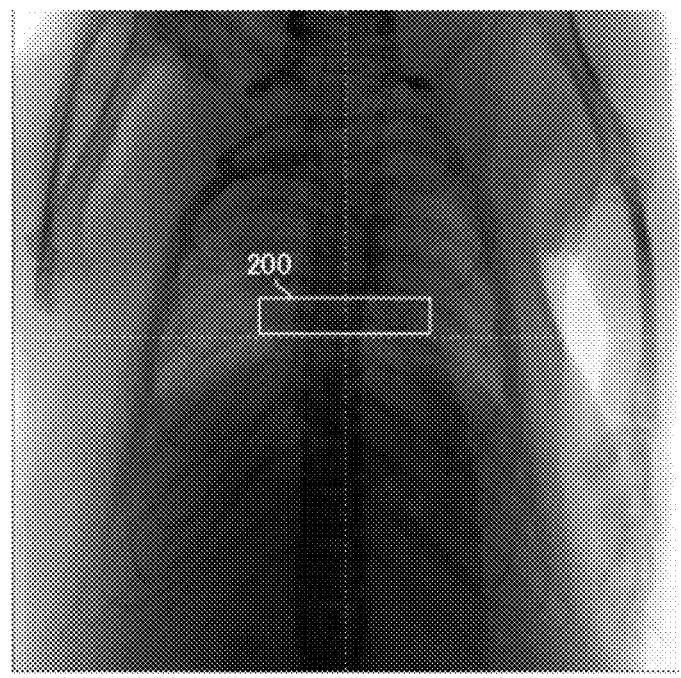
FIG. 6A is a view illustrating a fluoroscopic image at a scanning angle of 0° and a position of the ROI for synchronization.
Figure 6B:
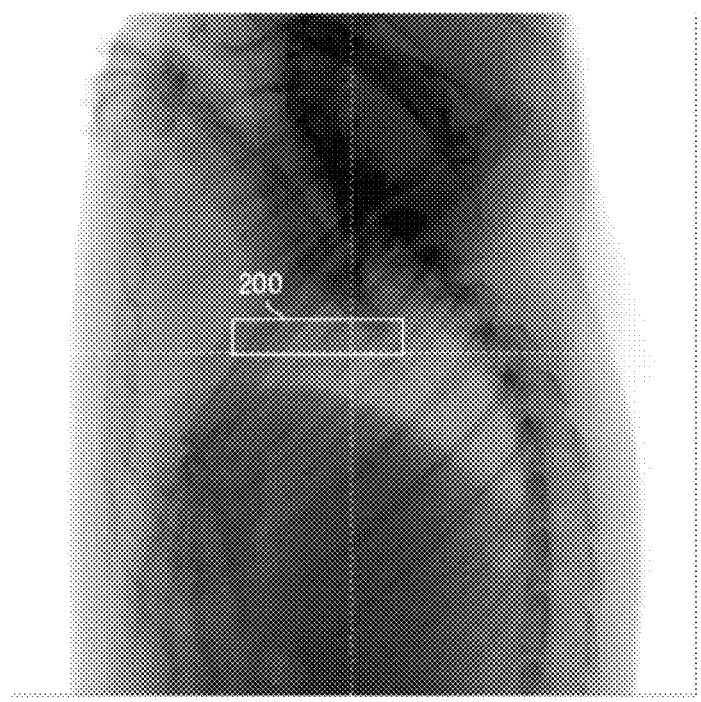
FIG. 6B is a view illustrating the fluoroscopic image at a scanning angle of 90° and the position of the ROI for synchronization.

FIGS. 6A and 6B are views illustrating the positions of the projection data and the ROI 200 for synchronization at the scanning angles of 0° and 90°, respectively. As described above, the position and the shape of the ROI 200 for synchronization on the projection data are different according to the scanning angle. As a result, the ROI 200 for synchronization can be calculated so as to track the portion which performs a periodic motion, and the heartbeat can be reliably captured with the characteristic amount in the ROI for synchronization.

(Verification of Setting of ROI for Synchronization)

Figure 7:
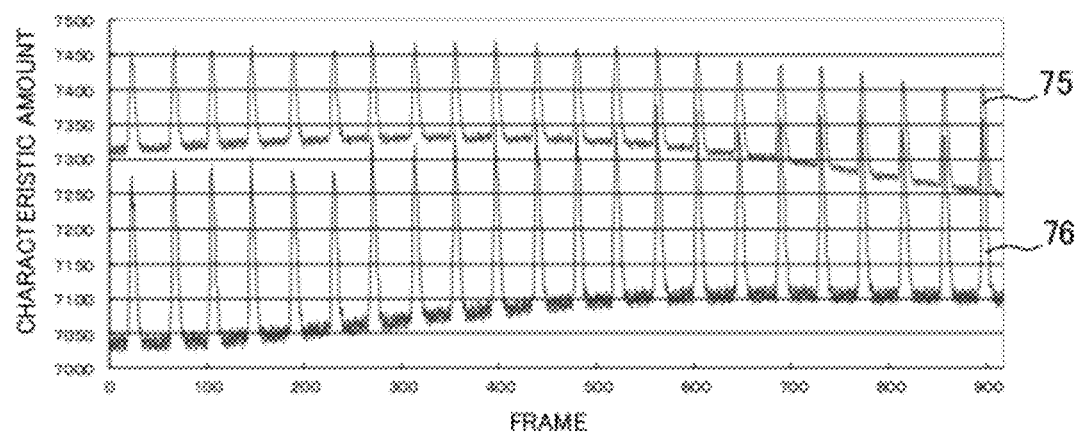
FIG. 7 is a graph illustrating a characteristic amount of the ROI for synchronization with respect to the scanning angle.

The characteristic amount was compared between a case in which the position and the size of the ROI for synchronization is not changed in accordance with the scanning angle and a case in which they are changed in accordance with the setting at a plurality of angles. FIG. 7 is a graph illustrating the characteristic amount of the ROI for synchronization to the scanning angle. In FIG. 7, in a graph 75 in which the position and the size of the ROI for synchronization is not changed in accordance with the scanning angle, the breathing beat signal having a size that could be sufficiently processed can be detected, but the heartbeat signal was small and not sufficient. On the other hand, in a graph 76 of a case in which the ROI for synchronization is changed in accordance with the setting at a plurality of angles, both the breathing beat signal and the heartbeat signal could be detected with the sizes that can be sufficiently processed. As described above, it was verified that the ROI for synchronization can detect sufficient breathing beat and heartbeat by tracking the movement of the portion to be synchronized with in accordance with the scanning angle rather than by fixing on a certain position on the projection data.

(Calculation Principle of Interpolation of ROI for Synchronization)

Figure 8A:
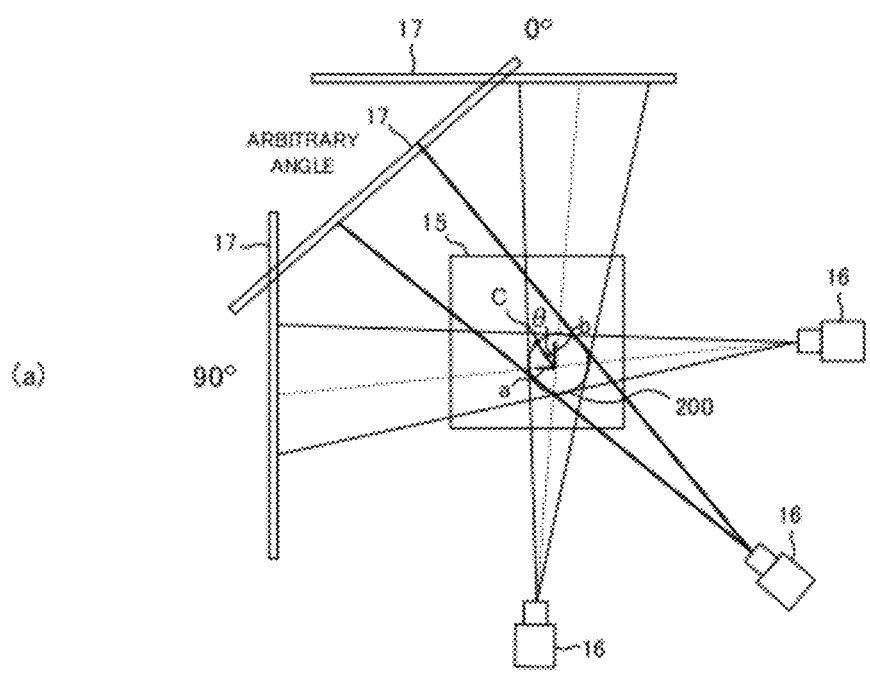
FIG. 8A is a side fluoroscopic diagram of a scanning portion.
Figure 8B:
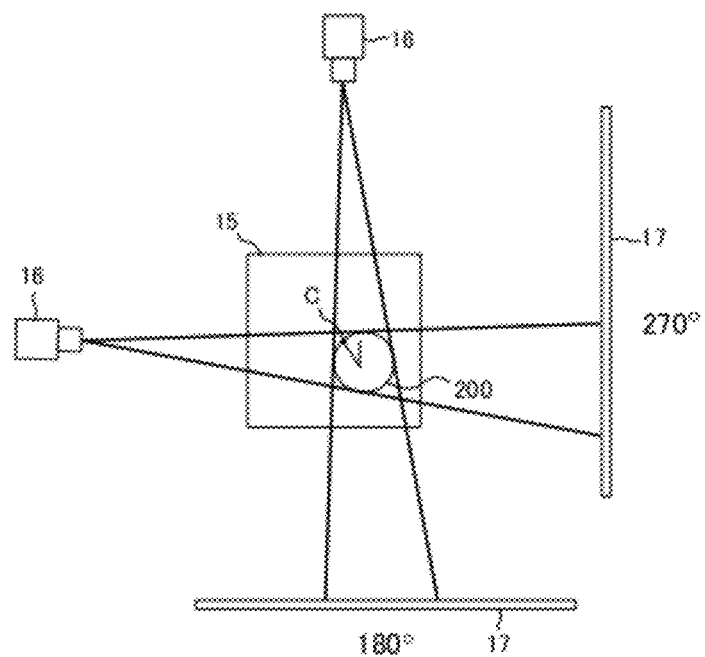
FIG. 8B is a side fluoroscopic diagram of the scanning portion.

Subsequently, the calculation principle of the ROI for synchronization will be described. FIGS. 8A and 8B are side fluoroscopic diagrams of a scanning unit. As illustrated in FIG. 8, first, by setting the ROI 200 for synchronization at each of the scanning angles of 0° and 90°, the center positions of the ROI 200 for synchronization at each of the scanning angles of 0° and 90° can be acquired. Since the rotation center C is known, a distance between the rotation center C and the center position of the ROI 200 for synchronization at each scanning angle can be acquired. Supposing that the distance between the rotation center C and the center position of the ROI for synchronization at each of the scanning angles of 0° and 90° is a bottom side length b and an opposite side length a, an angle □ of the center position of the ROI for synchronization can be acquired by using □=a tan (a/b) from the Pythagorean theorem. Moreover, an oblique side length h can be also acquired by h=O(a2+b2).

Then, the scanning angle of the current frame can be calculated from the number of current frames/total frames, and supposing that the scanning angle of this current frame is an arbitrary angle, the 0° direction coordinate x at the center of the ROI for synchronization can be acquired by x=h·cos(□+arbitrary angle). Moreover, the 90° direction coordinate y at the center of the ROI 200 for synchronization can be acquired by y=h·sin(□+arbitrary angle). As described above, the frame of the ROI 200 for synchronization is calculated from the 0° direction coordinate x and the 90° direction coordinate y of the center. Then, the position and the shape of the ROI for synchronization at an arbitrary angle can be calculated from the shape of the ROI 200 for synchronization set at the position coordinate (x, y) of the center at each of the scanning angles of 0° and 90°. For example, the position and the shape of the ROI 200 for synchronization at the scanning angles of 180° and 270° as illustrated in FIG. 8B, for example, can be calculated.

It may be configured that the portion moving periodically is automatically recognized and the portion is automatically recognized and followed each time the scanning angle of the gantry is moved so as to calculate the ROI for synchronization at each angle without setting the ROI for synchronization. In this case, the ROI for synchronization is determined by automatically recognizing the heart when the periphery of the subject is scanned and followed while a 360-degree rotation is made so that automatic face recognition follows the motion of a pet or a person by using a digital camera or the like. As a result, scanning during automatic recognition is made possible, and a result similar to the automatic adjustment on the basis of the scanning angles of 0° and 90° can be obtained.

(Trajectory of ROI for Synchronization)

Figure 9:
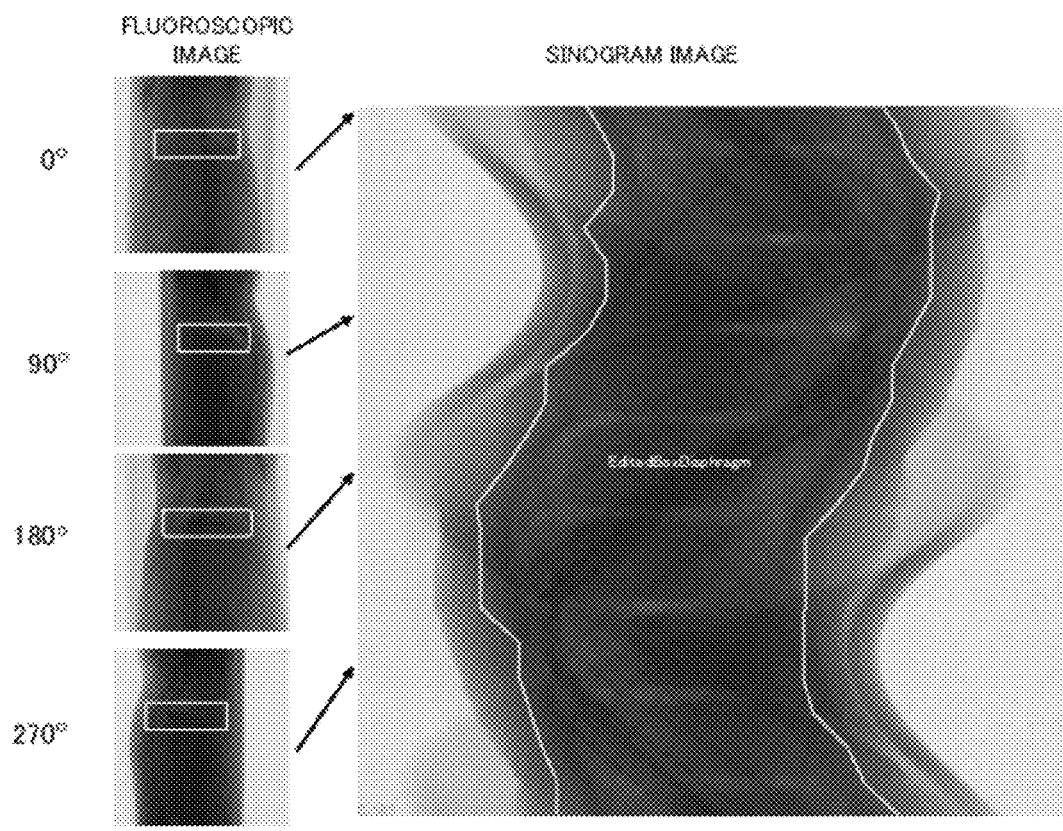
FIG. 9 is a view illustrating a sinogram image indicating a change in the ROI for synchronization with respect to the scanning angle.

Actually, as described above, a change in the position and the shape of the ROI 200 for synchronization in accordance with the scanning angle was calculated. FIG. 9 is a view illustrating a sinogram image indicating a change in the ROI 200 for synchronization to the scanning angle. As illustrated in FIG. 9, if the positions and the shapes of the ROI for synchronization at 0°, 90°, 180°, and 270° were overlapped for all the scanning angles, a helical sinogram image was obtained. That is, it is known that the calculated ROI for synchronization tracks the target portion in a suitable shape while drawing a helical trajectory in accordance with the change in the scanning angle.

(Breathing Synchronized Processing)

Figure 10A:
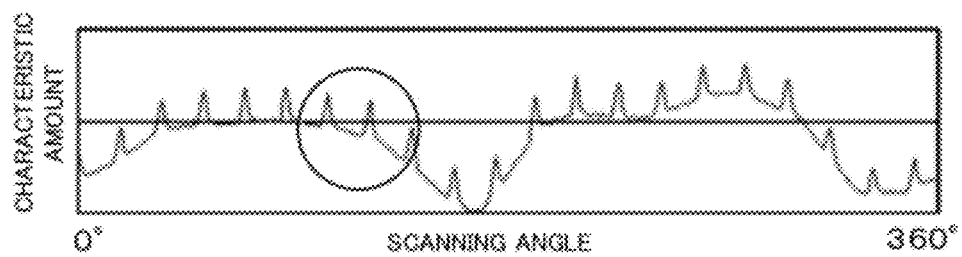
FIG. 10A is a graph illustrating the characteristic amount of the ROI for synchronization from the scanning angle of 0° to 360°.
Figure 10B:
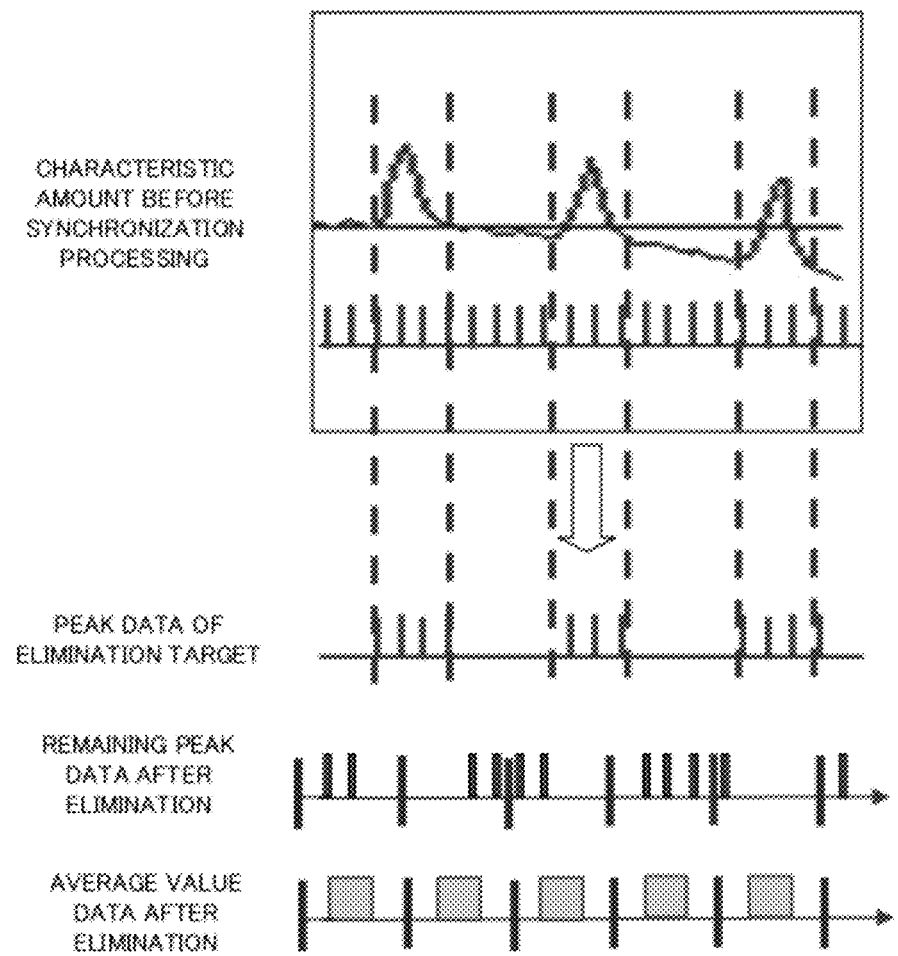
FIG. 10B is a diagram illustrating a processing procedure by using a part of the graph illustrating the characteristic amount of the ROI for synchronization from the scanning angle of 0° to 360°.

Subsequently, the breathing synchronized processing will be described. FIG. 10A is a graph indicating the characteristic amount of the ROI for synchronization from the scanning angle 0° to 360°, and FIG. 10B is a diagram illustrating a processing procedure by using a part of the graph. As illustrated in FIG. 10A, the characteristic amount of the ROI for synchronization changes so as to generate a peak indicating the lung diastole on a gentle periodic curve with respect to a change in the scanning angle. In the breathing synchronized processing, it is preferable that the data of a peak indicating the lung diastole is eliminated and the lung systole is specified by the remaining data for reconstruction of a three-dimensional image. The ROI for synchronization can be set so as to track the target portion to be synchronized with by means of such calculation. Then, the processing synchronized with a periodic motion of the portion can be reliably executed.

As illustrated in FIG. 10B, data of the peak indicating the lung diastole is eliminated and data of the eliminated peak section is interpolated by the remaining data. At that time, the predetermined scanning angle and the projection data are interpolated in association with each other. The projection data of a specific scanning angle may be interpolated by an average value by using the projection data of a nearby scanning angle. The projection data used in the processing can be preferably used for 3600 frames or more in a single rotation. The eliminated data can be easily interpolated by using many pieces of data.

(Peak Elimination Processing)

The details of the processing of eliminating the data of a peak indicating the lung diastole as described above will be described. A scanning angle in which an absolute value of a differential value of a characteristic amount by the scanning angle is larger than a threshold value can be determined to be a peak of breathing beat. Since the breathing beat peak is extremely larger than the heartbeat peak, the phase sections can be sorted on the basis of such determination. The threshold value can be appropriately set by grasping the differential value of the characteristic amount for the projection data scanned by a user on a trial basis. In actual peak elimination processing, an appropriate condition is preferably set with allowance such that 3° above and below the scanning angle at which the differential value larger than the threshold value is obtained or the like, for example.

(Verification Result of Peak Elimination Processing)

Figure 11:
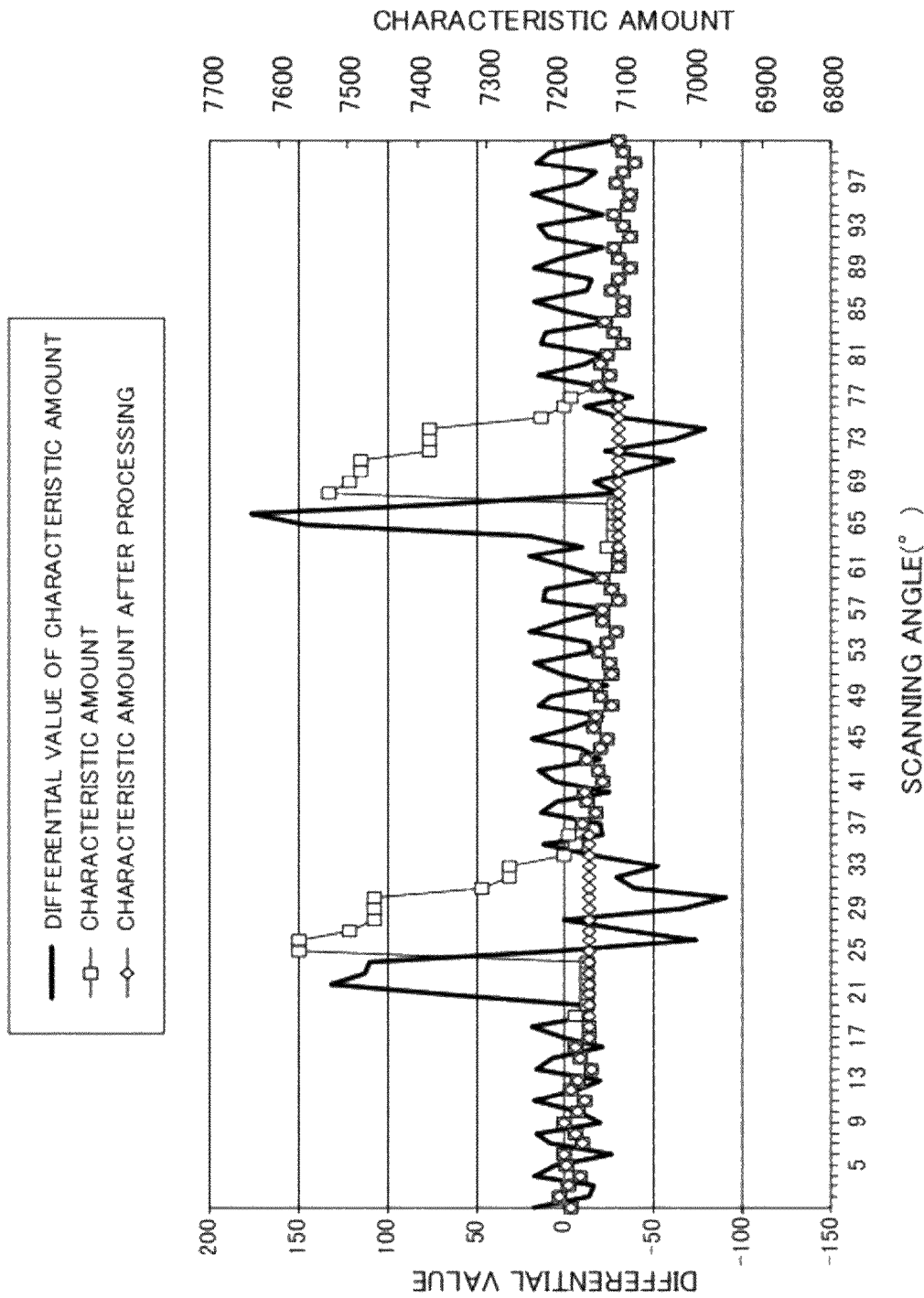
FIG. 11 is a graph illustrating the characteristic amount of the ROI for synchronization with respect to the scanning angle, a differential value for the scanning angle of the characteristic amount, and the characteristic amount after interpolation.

The above-described peak elimination processing was applied to the actually scanned projection data. FIG. 11 is a graph illustrating a characteristic amount of the ROI for synchronization to the scanning angle, a differential value for the scanning angle of the characteristic amount, and the characteristic amount after interpolation. As illustrated in FIG. 11, the differential value of the characteristic amount is obviously larger in the vicinity of the peak indicating the lung diastole. Thus, the scanning angle with the differential value larger than 50 and several degrees before and after that are set as a range of the scanning angle corresponding to a peak and the data was eliminated, and the eliminated peak portion was interpolated by the projection data of the other scanning angles. As a result, data of only the lung systole can be left, and three-dimensional CT image data of the lung systole can be reconstructed.

Figure 12A:
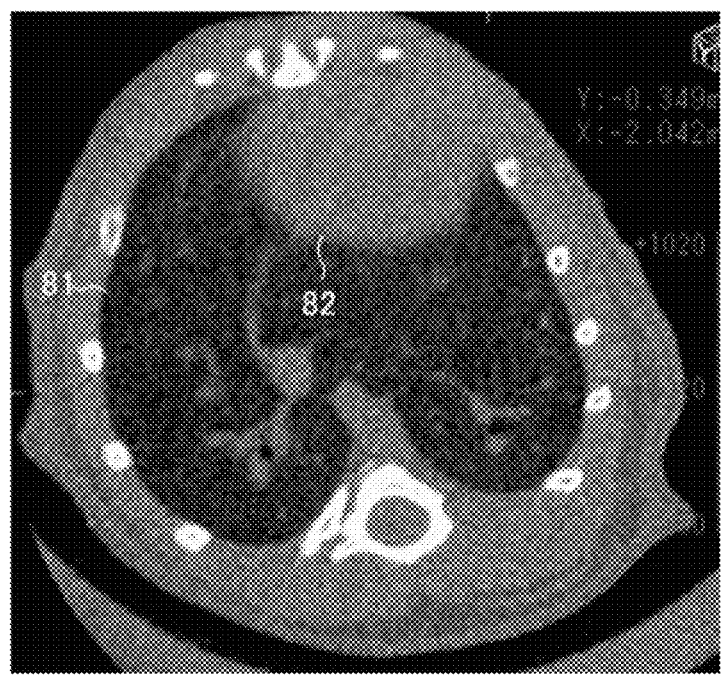
FIG. 12A is a view illustrating a sectional image of a trunk of a mouse when the breathing synchronized processing is not executed.
Figure 12B:
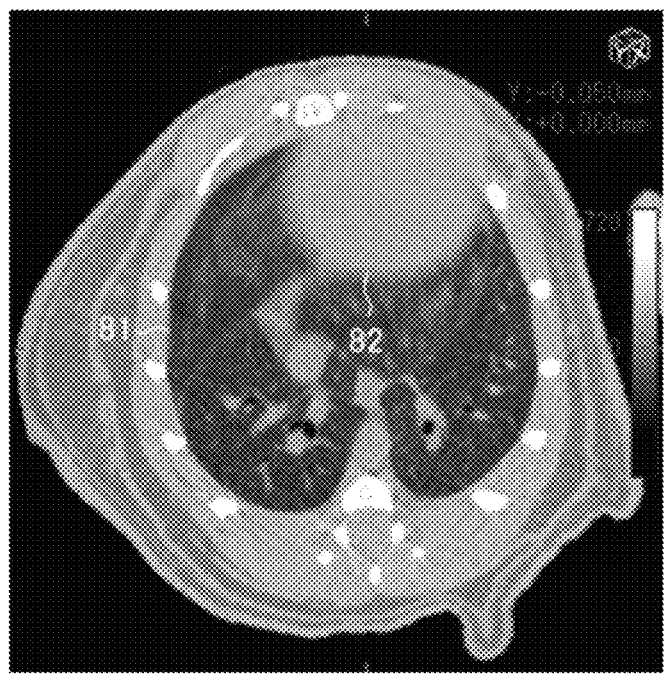
FIG. 12B is a view illustrating a sectional image of a trunk of a mouse when the breathing synchronized processing is executed.

FIG. 12A is a view illustrating a sectional image of a trunk of a mouse when the breathing synchronized processing is not executed. FIG. 12B is a view illustrating a sectional image of a trunk of a mouse when the breathing synchronized processing is executed. In FIG. 12A, each portion in an internal organ 81 displayed in the section is blurred but in FIG. 12B, each portion in the internal organ 81 is displayed clearly. However, since heartbeat synchronized processing is not executed, a heart 82 is displayed unclearly in both figures.

(Heartbeat Synchronized Processing)

Figure 13:
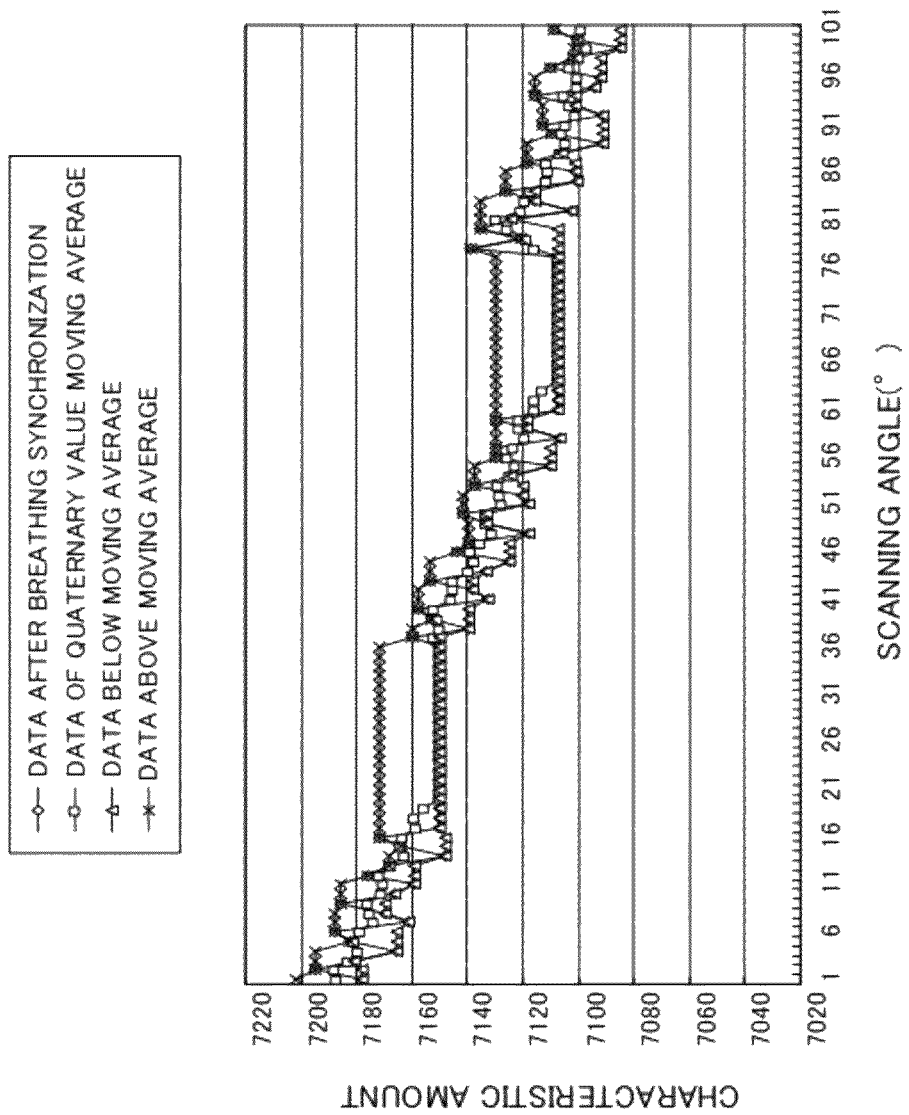
FIG. 13 is a graph of the characteristic amount for indicating a procedure of heartbeat synchronized processing.

Subsequently, the heartbeat synchronized processing will be described. FIG. 13 is a graph of a characteristic amount for explaining a procedure of the heartbeat synchronized processing. As illustrated in FIG. 13, a peak with a short period due to the heartbeat is generated in the graph of the characteristic amount from which the berating peak is eliminated. For this data, moving average of the characteristic amount by each scanning angle is calculated. The calculation condition for the moving average can be set appropriately by a user, but quaternary moving average is preferable.

Then, if the characteristic amount of a specific scanning angle is larger than the moving average, it is determined to be the heart diastole, while if the amount is smaller than the moving average, it is determined to be the heart systole. As described above, the projection data can be sorted and extracted by the phase section of the heart diastole and systole by means of the heartbeat synchronized processing. Since an abnormal value can easily occur in a value at the end of the angle range of scanning angles emptied by peak elimination when the moving average is used, a center value is preferably used.

If an offset from the moving average value is set in advance, an allowance is given for above and below the moving average and the data larger or smaller than the offset is sorted to the phase section of the heart diastole and systole, data can be collected more accurately. Particularly, if the scanning frame speed is raised to 100 fps, for example, it is effective to raise the threshold value.

(Verification Result of Heartbeat Synchronized Processing)

As the result of the above-described heartbeat synchronized processing for the data actually subjected to the breathing synchronized processing, a graph of the characteristic amount is illustrated in FIG. 13. In FIG. 13, the data after the breathing synchronization is indicated by diamonds, and the data of the moving average is indicated by regular squares. Moreover, the data below the moving average is indicated by triangles and the data above the moving average is indicated by crosses. As illustrated in FIG. 13, the position of the data after the heartbeat synchronized processing, that is, higher or lower than the moving average of the characteristic amount can be clearly determined. As described above, the data of the heart diastole and systole can be clearly sorted.

Figure 14:
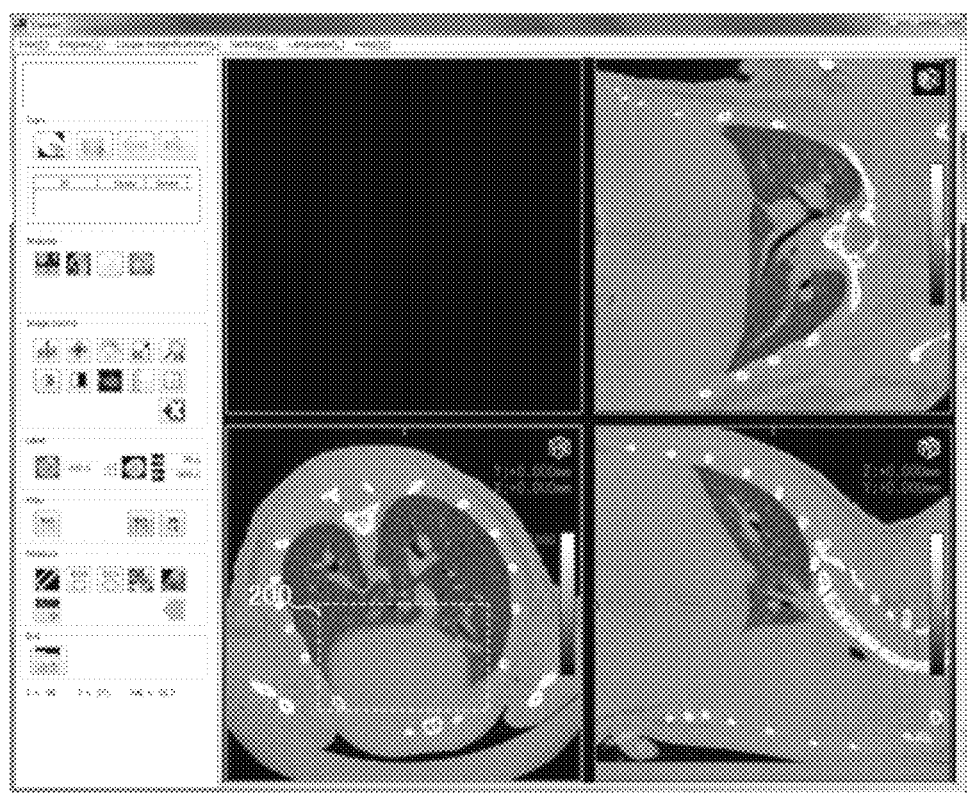
FIG. 14 is a view illustrating an image example without the heartbeat synchronized processing.
Figure 15:
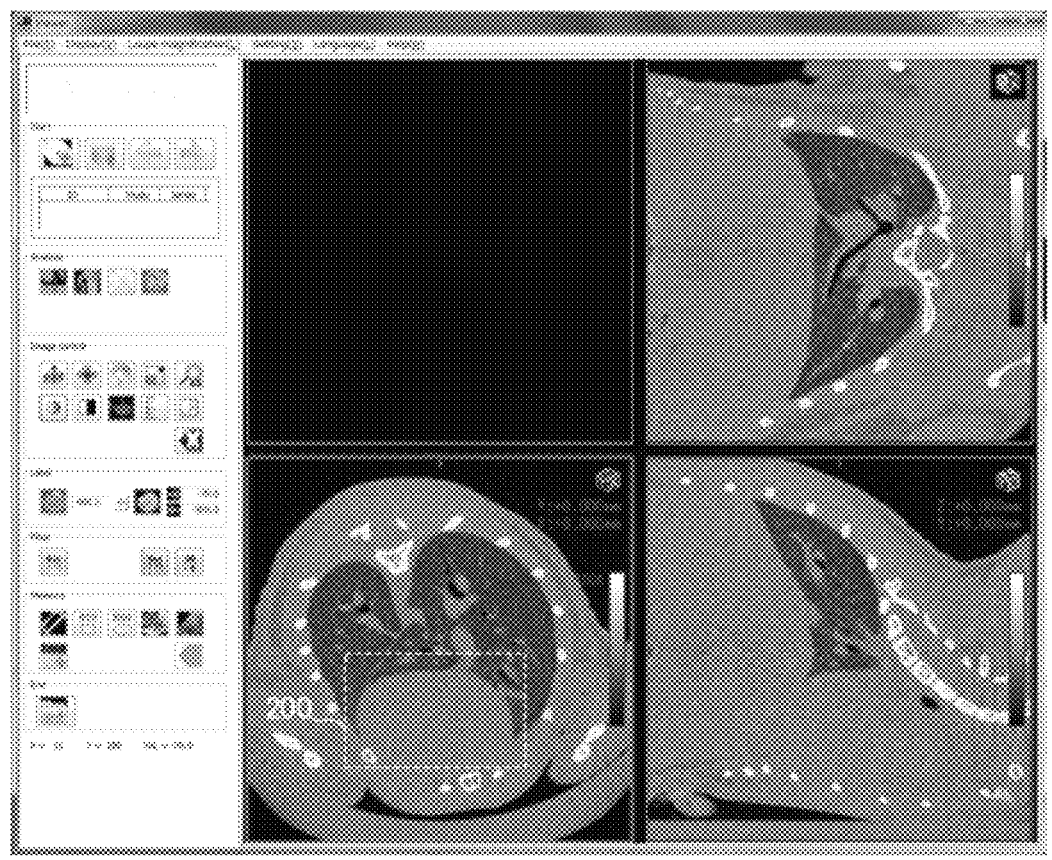
FIG. 15 is a view illustrating a CT image example obtained by specifying projection data of diastole of a heart by the heartbeat synchronized processing and image reconstruction.
Figure 16:
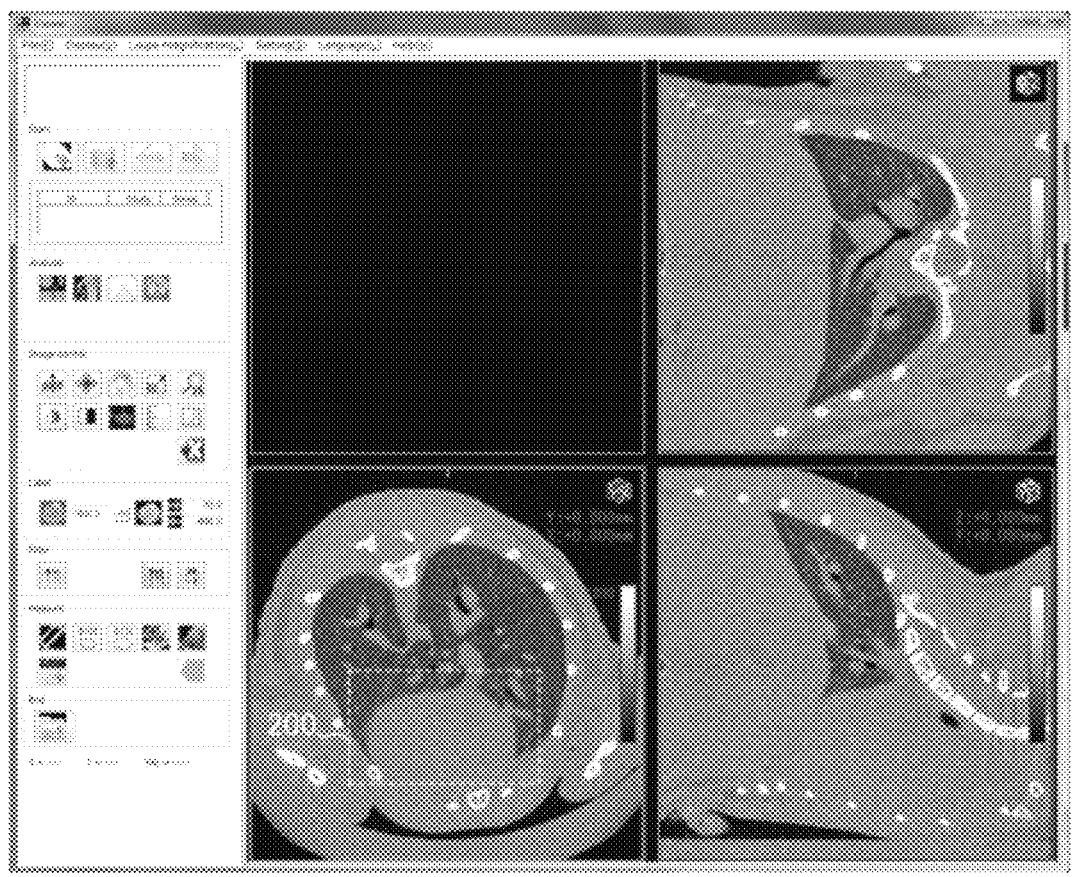
FIG. 16 is a view illustrating a CT image example obtained by specifying projection data of systole of a heart by the heartbeat synchronized processing and image reconstruction.

The heartbeat synchronized processing was executed, and image reconstruction was performed for each data of the heart diastole and systole. FIG. 14 is a view illustrating an image example without the heartbeat synchronized processing. FIG. 15 is a view illustrating an image example in which the projection data of the heart diastole is extracted by the heartbeat synchronized processing and subjected to image reconstruction. FIG. 16 is a view illustrating an image example in which the projection data of the heart systole is extracted by the heartbeat synchronized processing and subjected to image reconstruction. In FIG. 14, a boundary of the heart is not clear, while in FIGS. 15 and 16, the boundary of the heart is clearly displayed. As described above, it was demonstrated that clear reconstructed images can be obtained both for the heart diastole and systole by the heartbeat synchronized processing. As a result, injection amount, capacity rate and the like of the heart can be accurately calculated.

What is claimed is:

1. A CT image processing device which processes X-ray projection data in synchronization with a periodic motion of a portion of a subject, comprising:
   an ROI calculating unit configured to calculate, using the X-ray projection data, specific information on ROI for synchronization for each scanning angle so as to track the portion of the subject to be synchronized with, wherein
   the periodic motion of the portion of the subject is detected from the ROI for synchronization specified by the specific information, and the X-ray projection data is reconstructed into CT image data according to the detected periodic motion.

2. The CT image processing device according to claim 1, wherein
   the ROI calculating unit calculates the specific information of ROI for synchronization for the projection data of other scanning angles on the basis of the ROI for synchronization set for fluoroscopic data of a plurality of scanning angles.

3. The CT image processing device according to claim 1, further comprising:

an ROI setting unit configured to store the ROI for synchronization set for the projection data of a plurality of scanning angles in association with the projection data during scanning.

4. A CT image processing device which processes X-ray projection data in synchronization with a periodic motion of a portion of a subject, comprising:
an ROI calculating unit configured to calculate specific information on ROI for synchronization for each scanning angle so as to track the portion of the subject to be synchronized with, wherein
the ROI calculating unit calculates, as the specific information of ROI for synchronization for the projection data of other scanning angles, a position and a shape of the ROI for synchronization by referring to the position of a rotation center of X-ray irradiation on the projection data on the basis of the ROI for synchronization set for fluoroscopic data of a plurality of scanning angles.

5. A CT image processing device which processes X-ray projection data in synchronization with a periodic motion of a portion of a subject, comprising:
an ROI calculating unit configured to calculate specific information on ROI for synchronization for each scanning angle so as to track the portion of the subject to be synchronized with, wherein
the ROI calculating unit calculates the specific information of ROI for synchronization for projection data of other scanning angles on the basis of the ROI for synchronization set respectively for projection data of two scanning angles forming an angle of 90° with each other.

6. A CT image processing device which processes X-ray projection data in synchronization with a periodic motion of a portion of a subject, comprising:
an ROI calculating unit configured to calculate specific information on ROI for synchronization for each scanning angle so as to track the portion of the subject to be synchronized with; and
a breathing synchronized processing unit configured to sort each projection data into a predetermined phase segment of breathing beat on the basis of a relationship between the scanning angle and a characteristic amount of the ROI for synchronization.

7. The CT image processing device according to claim 6, wherein
the breathing synchronized processing unit differentiates the characteristic amount of the ROI for synchronization by the scanning angle and sorts and extracts the projection data on the basis of a predetermined threshold value using the differential value.

8. The CT image processing device according to claim 6, further comprising:
a heartbeat synchronized processing unit configured to sort and extract the projection data stored into the predetermined phase segment of breathing beat into a predetermined phase segment of heartbeat on the basis of a relationship between the scanning angle and the characteristic amount of the ROI for synchronization.

9. The CT image processing device according to claim 8, wherein
the heartbeat synchronized processing unit calculates a moving average value of the characteristic amount of the ROI for synchronization with respect to the scanning angle for the projection data sorted into the predetermined phase segment of breathing beat and sorts and extracts the projection data on the basis of the moving average value.

10. The CT image processing device according to claim 6, further comprising:
an image reconstruction unit configured to reconstruct CT image data by the projection data sorted into the predetermined phase segment of breathing beat or heartbeat.

11. The CT image processing device according to claim 10, wherein
the image reconstruction unit reconstructs the CT image by interpolating the projection data missing due to the sorting of the projection data with projection data at the adjacent scanning angle.

12. The CT image processing device according to claim 11, wherein
the image reconstruction unit uses the projection data averaged for a plurality of pieces of data having the scanning angles close to each other for reconstruction of the CT image data as projection data with respect to averaged scanning angle.

13. A CT image processing method for processing X-ray projection data in synchronization with a periodic motion of a portion of a subject by using a computer, comprising the step of
calculating, using the X-ray projection data, specific information on ROI for synchronization is executed for each scanning angle so as to track the portion of the subject to be synchronized with, wherein
the periodic motion of the portion of the subject is detected from the ROI for synchronization specified by the specific information, and the X-ray projection data is reconstructed into CT image data according to the detected periodic motion.

* * * * *